United States Patent
Rulkov et al.

(10) Patent No.: US 7,468,036 B1
(45) Date of Patent: *Dec. 23, 2008

(54) MONITORING DEVICE, METHOD AND SYSTEM

(75) Inventors: Nikolai Rulkov, San Diego, CA (US);
Mark Hunt, San Diego, CA (US);
Donald Brady, Las Vegas, NV (US);
Steve Lui, San Diego, CA (US); Sammy I. Elhag, San Diego, CA (US)

(73) Assignee: Impact Sports Technology, Inc., Las Vegas, NV (US)

( * ) Notice: Subject to any disclaimer, the term of this patent is extended or adjusted under 35 U.S.C. 154(b) by 37 days.

This patent is subject to a terminal disclaimer.

(21) Appl. No.: 11/762,078

(22) Filed: Jun. 13, 2007

Related U.S. Application Data

(63) Continuation-in-part of application No. 11/566,229, filed on Dec. 3, 2006, which is a continuation-in-part of application No. 11/388,707, filed on Mar. 24, 2006, which is a continuation-in-part of application No. 11/085,778, filed on Mar. 21, 2005.

(60) Provisional application No. 60/829,679, filed on Oct. 17, 2006, provisional application No. 60/843,967, filed on Sep. 12, 2006, provisional application No. 60/665,116, filed on Mar. 25, 2005, provisional application No. 60/613,785, filed on Sep. 28, 2004.

(51) Int. Cl.
*A61B 5/00* (2006.01)
(52) U.S. Cl. .................. 600/485; 600/500; 600/503
(58) Field of Classification Search .................. None
See application file for complete search history.

(56) References Cited

U.S. PATENT DOCUMENTS

| | | | |
|---|---|---|---|
| 4,380,240 A | 4/1983 | Jobsis et al. | |
| 4,800,495 A | 1/1989 | Smith | |
| 4,807,630 A | 2/1989 | Malinouskas | |
| 4,825,879 A | 5/1989 | Tan et al. | |
| 5,213,099 A | 5/1993 | Tripp, Jr. | |
| 5,431,170 A | 7/1995 | Mathews | |
| 5,735,800 A | 4/1998 | Yasukawa et al. | |
| 6,018,673 A | 1/2000 | Chin et al. | |
| 6,241,684 B1 * | 6/2001 | Amano et al. | 600/531 |
| 6,470,199 B1 | 10/2002 | Kopotic et al. | |
| 6,556,852 B1 | 4/2003 | Schulze et al. | |
| 6,575,912 B1 * | 6/2003 | Turcott | 600/485 |
| 6,599,251 B2 | 7/2003 | Chen et al. | |
| 6,605,038 B1 | 8/2003 | Teller et al. | |
| 6,616,613 B1 * | 9/2003 | Goodman | 600/504 |
| 6,678,543 B2 | 1/2004 | Diab et al. | |
| 6,681,454 B2 | 1/2004 | Modgil et al. | |

(Continued)

*Primary Examiner*—Robert L Nasser
(74) *Attorney, Agent, or Firm*—Clause Eight LLP; M. Catania

(57) ABSTRACT

A monitoring device (20) for monitoring the vital signs of a user is disclosed herein. The monitoring device (20) is preferably an article (25) having an optical sensor (30) and a circuitry assembly (35). The optical sensor (30) preferably comprises a photodetector (130) and a plurality of light emitting diodes (135). The monitoring device (20) preferably provides for the display of the following information about the user: pulse rate; blood oxygenation levels; calories expended by the user of a pre-set time period; target zones of activity; time; distance traveled; and/or dynamic blood pressure.

6 Claims, 13 Drawing Sheets

U.S. PATENT DOCUMENTS

| | | |
|---|---|---|
| 6,720,734 B2 | 4/2004 | Norris |
| 6,808,473 B2 | 10/2004 | Hisano et al. |
| 6,813,511 B2 | 11/2004 | Diab et al. |
| 6,866,639 B2 * | 3/2005 | Causevic et al. ............ 600/559 |
| 7,179,228 B2 | 2/2007 | Banet |
| 2002/0109600 A1 | 8/2002 | Mault et al. |
| 2006/0084851 A1 * | 4/2006 | Lee et al. .................... 600/301 |
| 2007/0244398 A1 * | 10/2007 | Lo et al. ..................... 600/500 |
| 2007/0287923 A1 * | 12/2007 | Adkins et al. ............... 600/485 |

* cited by examiner

MONITORING DEVICE, METHOD AND SYSTEM

CROSS REFERENCES TO RELATED APPLICATIONS

The Present application is a continuation-in-part application of U.S. patent application Ser. No. 11/566,229, filed on Dec. 3, 2006, which is a continuation-in-part application of U.S. patent application Ser. No. 11/388,707, filed on Mar. 24, 2006, which claims priority to U.S. Provisional Application No. 60/665,116, filed on Mar. 25, 2005, now abandoned; and the Present application is a continuation-in-part application of U.S. patent application Ser. No. 11/085,778, filed on Mar. 21, 2005, which claims priority to U.S. Provisional Application No. 60/613,785, filed on Sep. 28, 2004, now abandoned. The Present application also claims priority to U.S. Provisional Application No. 60/843,967, filed on Sep. 12, 2006 and U.S. Provisional Application No. 60/829,679, filed on Oct. 17, 2006.

STATEMENT REGARDING FEDERALLY SPONSORED RESEARCH OR DEVELOPMENT

Not Applicable

BACKGROUND OF THE INVENTION

1. Field of the Invention

The present invention is related to real-time vital sign monitoring devices. More specifically, the present invention relates to a device for monitoring a user's vital signs.

2. Description of the Related Art

There is a need to know how one is doing from a health perspective. In some individuals, there is a daily, even hourly, need to know one's health. The prior art has provided some devices to meet this need.

One such device is a pulse oximetry device. Pulse oximetry is used to determine the oxygen saturation of arterial blood. Pulse oximeter devices typically contain two light emitting diodes: one in the red band of light (660 nanometers) and one in the infrared band of light (940 nanometers). Oxyhemoglobin absorbs infrared light while deoxyhemoglobin absorbs visible red light. Pulse oximeter devices also contain sensors that detect the ratio of red/infrared absorption several hundred times per second. A preferred algorithm for calculating the absorption is derived from the Beer-Lambert Law, which determines the transmitted light from the incident light multiplied by the exponential of the negative of the product of the distance through the medium, the concentration of the solute and the extinction coefficient of the solute.

The major advantages of pulse oximetry devices include the fact that the devices are non-invasive, easy to use, allows for continuous monitoring, permits early detection of desaturation and is relatively inexpensive. The disadvantages of pulse oximetry devices are that it is prone to artifact, it is inaccurate at saturation levels below 70%, and there is a minimal risk of burns in poor perfusion states. Several factors can cause inaccurate readings using pulse oximetry including ambient light, deep skin pigment, excessive motion, fingernail polish, low flow caused by cardiac bypass, hypotension, vasoconstriction, and the like.

Chin et al., U.S. Pat. No. 6,018,673 discloses a pulse oximetry device that is positioned entirely on a user's nail to reduce out of phase motion signals for red and infrared wavelengths for use in a least squares or ratio-of-ratios technique to determine a patient's arterial oxygen saturation.

Smith, U.S. Pat. No. 4,800,495 discloses an apparatus for processing signals containing information concerning the pulse rate and the arterial oxygen saturation of a patient. Smith also discloses maintaining the position of the LEDs and detectors to prevent motion-artifacts from being produced in the signal.

Another method for using a pulse oximeter to measure blood pressure is disclosed in U.S. Pat. No. 6,616,613 to Goodman for a 'Physiological Signal Monitoring System'. The '613 patent discloses processing a pulse oximetry signal in combination with information from a calibrating device to determine a patient's blood pressure.

Chen et al, U.S. Pat. No. 6,599,251 discloses a system and method for monitoring blood pressure by detecting pulse signals at two different locations on a subjects body, preferably on the subject's finger and earlobe. The pulse signals are preferably detected using pulse oximetry devices.

Schulze et al., U.S. Pat. No. 6,556,852, discloses the use of an earpiece having a pulse oximetry device and thermopile to monitor and measure physiological variables of a user.

Malinouskas, U.S. Pat. No. 4,807,630, discloses a method for exposing a patient's extremity, such as a finger, to light of two wavelengths and detecting the absorbance of the extremity at each of the wavelengths.

Jobsis et al., U.S. Pat. No. 4,380,240 discloses an optical probe with a light source and a light detector incorporated into channels within a deformable mounting structure which is adhered to a strap. The light source and the light detector are secured to the patient's body by adhesive tapes and pressure induced by closing the strap around a portion of the body.

Tan et al., U.S. Pat. No. 4,825,879 discloses an optical probe with a T-shaped wrap having a vertical stem and a horizontal cross bar, which is utilized to secure a light source and an optical sensor in optical contact with a finger. A metallic material is utilized to reflect heat back to the patient's body and to provide opacity to interfering ambient light. The sensor is secured to the patient's body using an adhesive or hook and loop material.

Modgil et al., U.S. Pat. No. 6,681,454 discloses a strap that is composed of an elastic material that wraps around the outside of an oximeter probe and is secured to the oximeter probe by attachment mechanisms such as Velcro, which allows for adjustment after initial application without producing excessive stress on the spring hinge of the oximeter probe.

Diab et al., U.S. Pat. No. 6,813,511 discloses a disposable optical probe suited to reduce noise in measurements, which is adhesively secured to a patient's finger, toe, forehead, earlobe or lip.

Diab et al., U.S. Pat. No. 6,678,543 discloses an oximeter sensor system that has a reusable portion and a disposable portion. A method for precalibrating a light sensor of the oximeter sensor system is also disclosed.

Tripp, Jr. et al., U.S. Statutory Invention Registration Number H1039 discloses an intrusion free physiological condition monitor that utilizes pulse oximetry devices.

Hisano et al., U.S. Pat. No. 6,808,473, discloses a headphone-type exercise aid which detects a pulse wave using an optical sensor to provide a user with an optimal exercise intensity.

Mathews, U.S. Pat. No. 5,431,170 ("Mathews"), discloses a pulse responsive device, which has a pulse oximetry device (10) attached to a headband (12) and a separate read-out device (14) that may be attached to a glove and worn on the user's hand. Mathews discloses that the read-out device (14) has a digital display and an analogue display, however, Mathews provides no further detail.

Mault et al, U.S. Patent Application Publication Number 2002/0109600 ("Mault") discloses a smart activity monitor ("SAM") which is a pedometer based device which includes an electronic clock, a sensor, entry means for recording food consumption and exercise activities and a memory for storing such information. Mault fails to disclose the details of the display other than to mention that the SAM has a time display, an exercise display and a food display, with the exercise and food displays having a bar-graph style. Mault fails to disclose an optical sensor in detail, and only states that photo-plethysmography may be used to determine the heart rate by a sensor provided on the rear of a wrist mounted SAM.

Kopotic et al, U.S. Pat. No. 6,470,199, discloses a sock for positioning an optical probe.

Yasukawa et al., U.S. Pat. No. 5,735,800 ("Yasukawa"), discloses a wrist-worn device which is intended for limited motion about the user's wrist. Yasukawa discloses an optical sensor that uses a blue LED with a phototransistor in conjunction with an analog to digital converter to provide a digital signal to a data processing circuit.

In monitoring one's health there is a constant need to know how many calories have been expended whether exercising or going about one's daily routine. A calorie is a measure of heat, generated when energy is produced in our bodies. The amount of calories burned during exercise is a measure of the total amount of energy used during a workout. This can be important, since increased energy usage through exercise helps reduce body fat. There are several means to measure this expenditure of energy. To calculate the calories burned during exercise one multiplies the intensity level of the exercise by one's body weight (in kilograms). This provides the amount of calories burned in an hour. A unit of measurement called a MET is used to rate the intensity of an exercise. One MET is equal to the amount of energy expended at rest.

For example, the intensity of walking 3 miles per hour ("mph") is about 3.3 METS. At this speed, a person who weighs 132 pounds (60 kilograms) will burn about 200 calories per hour (60×3.3=198).

The computer controls in higher-quality exercise equipment can provide a calculation of how many calories are burned by an individual using the equipment. Based on the workload, the computer controls of the equipment calculate exercise intensity and calories burned according to established formulae.

The readings provided by equipment are only accurate if one is able to input one's body weight. If the machine does not allow this, then the "calories per hour" or "calories used" displays are only approximations. The machines have built-in standard weights (usually 174 pounds) that are used when there is no specific user weight.

There are devices that utilize a watch-type monitor to provide the wearer with heart rate as measured by a heartbeat sensor in a chest belt.

However, the prior art devices often suffer from noise, light and motion related problems. These problems are increased when the user participates in an athletic activity such as running. Further, attempting to correct one problem often creates additional problems such as increasing a sensor output which results in a shorter battery life.

The prior art has failed to provide a means for monitoring one's health that is accurate, easy to wear on one's body for extended time periods, allows the user to input information and control the output, and provides sufficient information to the user about the user's health. Thus, there is a need for a monitoring device that can be worn for an extended period and provide health information to a user.

BRIEF SUMMARY OF THE INVENTION

The present invention provides a solution to the shortcomings of the prior art. The present invention is accurate, comfortable to wear by a user for extended time periods, allows for input and controlled output by the user, is light weight, and provides sufficient real-time information to the user about the user's health.

One aspect of the present invention is a monitoring device for monitoring the health of a user. The monitoring device includes an article, an optical device for generating a pulse waveform, a circuitry assembly embedded within the article, a display member positioned on an exterior surface of the article, and a control means attached to the article.

The article is preferably a band to be worn on a user's wrist or ankle. The article preferably has a minimal mass, one to five ounces, and is flexible so that the user can wear it the entire day if necessary. The monitoring device allows the user to track calories burnt during a set time period, monitor heart rate, blood oxygenation levels, distance traveled, target zones and optionally dynamic blood pressure.

Yet another aspect of the present invention is a system for real time monitoring of a user's vital sign during a live event within a playing environment. The system includes a monitoring device, a computing device and an electro-optical display. The monitoring device is attached to an arm, wrist or ankle of the user. The monitoring device comprises means for generating a real-time vital sign signal corresponding to the heart rate of the user, and means for transmitting the real-time vital sign signal outside of the playing environment. The computing device is positioned outside of the playing environment. The computing device comprises means for receiving the real-time vital sign signal from the monitoring device, and means for processing the real-time vital sign signal for transmission to and image on the electro-optical display.

Yet another aspect of the present invention is a monitoring device for monitoring the health of a user. The monitoring device includes an article to be worn on the user's wrist, arm or ankle. The monitoring device also includes an optical sensor, a circuitry assembly, a display member and a control component. The optical sensor is disposed on the interior surface of the article. The circuitry assembly is preferably embedded within the annular body of the article. The display member is preferably attached to an exterior surface of the annular body of the article. The control component is disposed on the exterior surface of the annular body of the article. The control component controls the input of information and the output of information displayed on the display member.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
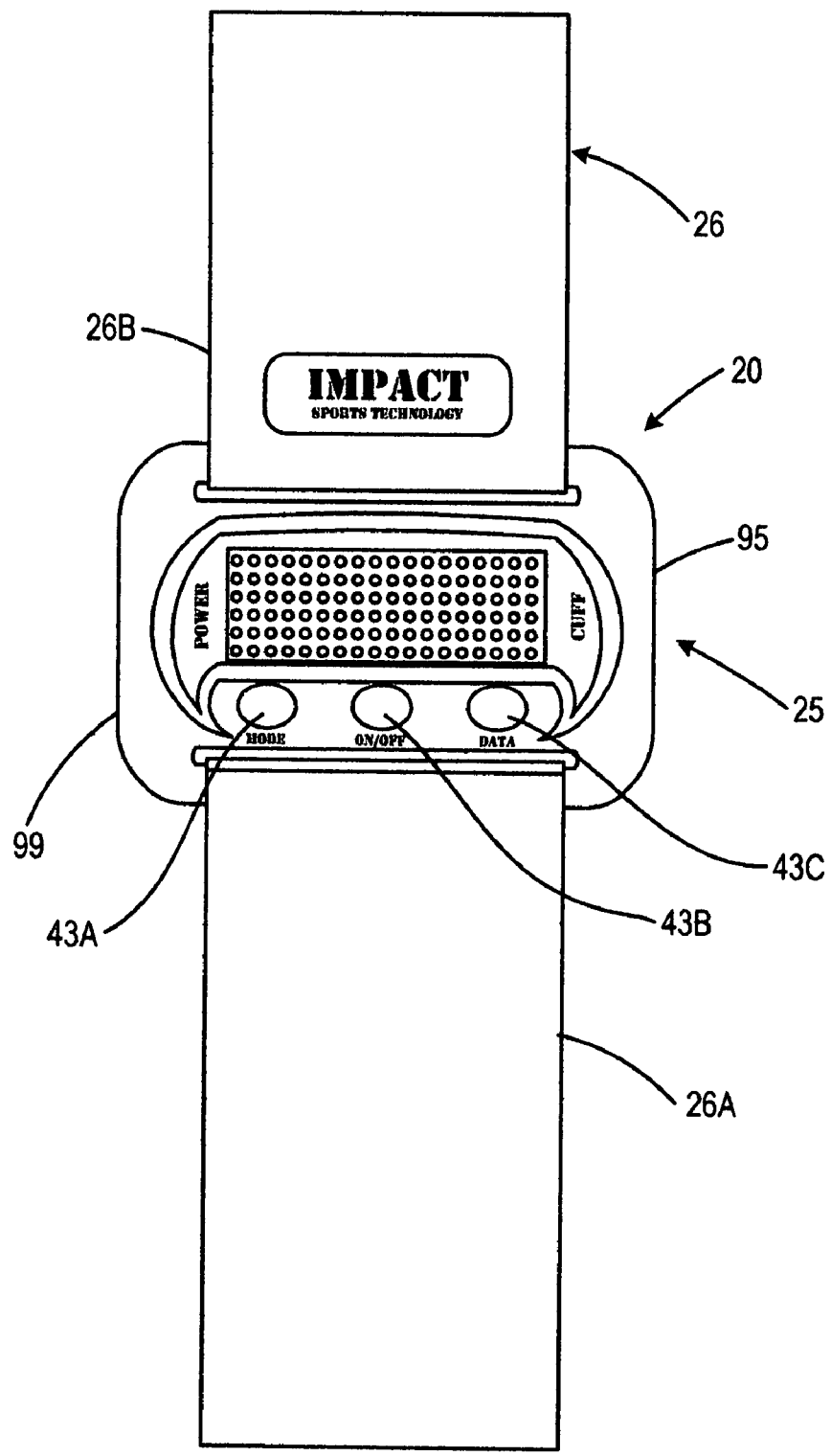
FIG. 1 is a plan view of a preferred embodiment of a monitoring device worn by a user.
Figure 2:
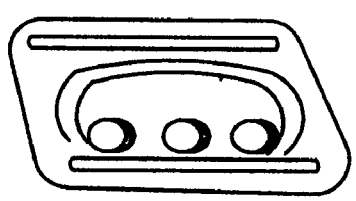
FIG. 2 is a perspective view of the article of the monitoring device worn by a user.
Figure 2A:
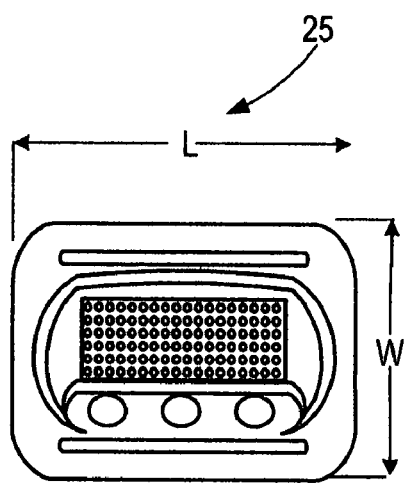
FIG. 2A is a plan view of the article of the monitoring device.
Figure 2B:
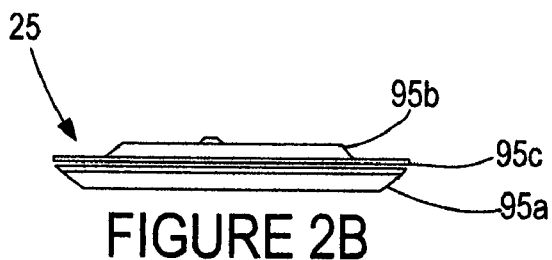
FIG. 2B is a front side view of the article of the monitoring device.
Figure 2D:
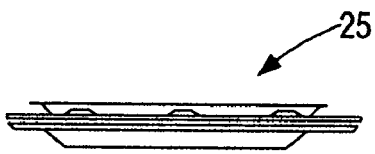
FIG. 2D is an edge side view of the article of the monitoring device.
Figure 2C:
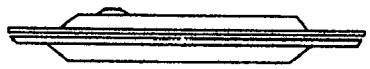
FIG. 2C is a rear side view of the article of the monitoring device.
Figure 2E:
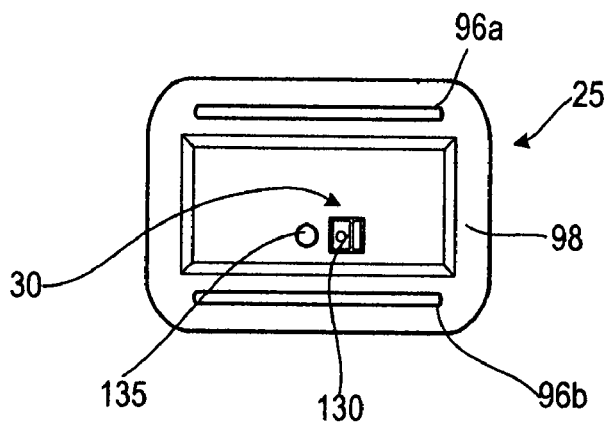
FIG. 2E is a bottom plan view of the article of the monitoring device.

As shown in FIGS. 1-2E, monitoring device is generally designated 20. The monitoring device 20 preferably includes an article 25 and an attachment band 26, preferably composed of first strap 26a and second strap 26b. The straps 26a and 26b are preferably attached to each other with a VELCRO® hook and loop material. The article 25 preferably includes an optical sensor 30, a circuitry assembly 35, control components 43a-43c and optionally a display member 40. The monitoring device 20 is preferably worn on a user's wrist 71, arm 72 or ankle 73. The article 25 preferably has a housing 95 that is sized to securely attach to a user's wrist 71, arm 72 or ankle 73, and the housing has an interior surface 98 and an exterior surface 99. The housing 95 also preferably has a pair of slots 96a and 96b for placement of the straps 96a and 96b therethrough for attachment purposes.

It is desirous to adapt the monitoring device 20 to the anatomy of the user's arm 72 or even the user's ankle. The strap 96 is preferably composed of neoprene, leather, synthetic leather, LYCRA, another similar material, or a combination thereof. The article 25 is preferably composed of a semi-rigid or rigid plastic with a rubber-like or semi-flex plastic bottom layer for contact with the user's body. The bottom layer of the housing 95 may have a curve surface for contact with a user's body. The article 25 preferably has a mass ranging from 5 grams to 50 grams. Preferably, the lower the mass of the article 25, the more comfort to the user. The article 25 preferably has a thickness ranging from 5 mm to 10 mm, and is most preferably 6.5 mm. The bottom layer 95a preferably has a thickness ranging from 3.0 mm to 5.0 mm, and most preferably is 3.3 mm. A top layer 95a preferably has a thickness ranging from 2.0 mm to 5.0 mm, and most preferably is 2.63 mm. A mid-layer 95c preferably has a thickness ranging from 0.25 mm to 1.0 mm, and most preferably is 0.5 mm. The housing 95 preferably has a width, W, ranging from 30 mm to 50 mm, more preferably from 35 mm to 45 mm, and is most preferably approximately 40 mm. The housing 95 preferably has a length, L, ranging from 40 mm to 65 mm, more preferably from 50 mm to 60 mm, and is most preferably approximately 55 mm. The article 25 preferably has a mass ranging from 5 grams to 50 grams, and more preferably from 10 grams to 40 grams. The light weight of the article 25 provides for more comfort to the user. The optical sensor 30 is preferably positioned on the interior surface 98 of the housing 95 and electrically connected to the circuitry assembly 35.

Although the monitoring device 20 is described in reference to an article worn on a user's arm, wrist or ankle, those skilled in the pertinent art will recognize that the monitoring device 20 may take other forms such as eyewear disclosed in U.S. patent application Ser. No. 11/566,228, which is hereby incorporated by reference in its entirety or a glove such as disclosed in U.S. patent application Ser. No. 11/473,641, which is hereby incorporated by reference in its entirety.

Figure 4:
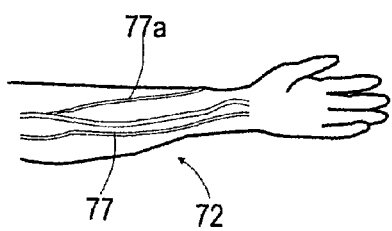
FIG. 4 is a schematic view of arteries within a human arm.

The optical sensor 30 of the monitoring device 20 is preferably positioned over the radial artery 77 or ulnar artery 77a (as shown in FIG. 4) if the article 25 is worn on the user's arm 72. The optical sensor 30 of the monitoring device 20 is preferably positioned over the posterior tibial artery of a user if the article 25 is worn on the user's ankle. However, those skilled in the pertinent art will recognize that the optical sensor may be placed over other arteries of the user without departing from the scope and spirit of the present invention. Further, the optical sensor 30 need only be in proximity to an artery of the user in order to obtain a reading or signal.

In a preferred embodiment, the optical sensor 30 is a plurality of light emitting diodes ("LED") 135 based on green light wherein the LEDs 135 generate green light (wavelength of 500-570 nm), and a photodetector 130 detects the green light. Yet in an alternative embodiment, the optical sensor 30 is a photodetector 130 and a single LED 135 transmitting light at a wavelength of approximately 900 nanometers as a pulsed infrared LED. Yet further, the optical sensor is a combination of a green light LED and a pulsed infrared LED to offset noise affects of ambient light and sunlight. As the heart pumps blood through the arteries in the user's arm, ankle or wrist, the photodetector 130, which is typically a photodiode, detects reflectance/transmission at the wavelengths (green, red or infrared), and in response generates a radiation-induced signal.

A preferred optical sensor 30 utilizing green light is a TRS1755 sensor from TAOS, Inc of Plano Tex. The TRS1755 comprises a green LED light source (567 nm wavelength) and a light-to-voltage converter. The output voltage is directly proportional to the reflected light intensity. Another preferred photodetector 130 is a light-to-voltage photodetector such as the TSL260R and TSL261, TSL261R photodetectors available from TAOS, Inc of Plano Texas. Alternatively, the photodetector 130 is a light-to-frequency photodetector such as the TSL245R, which is also available from TAOS, Inc. The light-to-voltage photodetectors have an integrated transimpedance amplifier on a single monolithic integrated circuit, which reduces the need for ambient light filtering. The TSL261 photodetector preferably operates at a wavelength greater than 750 nanometers, and optimally at 940 nanometers, which would preferably have a LED that radiates light at those wavelengths.

In a preferred embodiment, the circuit assembly 35 is flexible to allow for the contour of the user's arm, wrist or ankle, and the movement thereof. The circuitry assembly and display member 40 are preferably separate components electrically connected within the housing 95. In one embodiment, discussed below, the display member 40 is removed and the signal is sent to a device such as a personal digital assistant, laptop computer, mobile telephone, exercise equipment, or the like for display and even processing of the user's real-time vital signs information. Alternatively, the circuitry assembly 35 includes a flexible microprocessor board which is a low power, micro-size easily integrated board which provides blood oxygenation level, pulse rate (heart rate), signal strength bargraph, plethysmogram and status bits data. The microprocessor can also store data. The microprocessor can process the data to display pulse rate, blood oxygenation levels, calories expended by the user of a pre-set time period, target zone activity, time and dynamic blood pressure. Further, microprocessor preferably includes an automatic gain control for preventing saturation of the photodetector, which allows for the device to be used on different portions of the human body.

Figure 8:
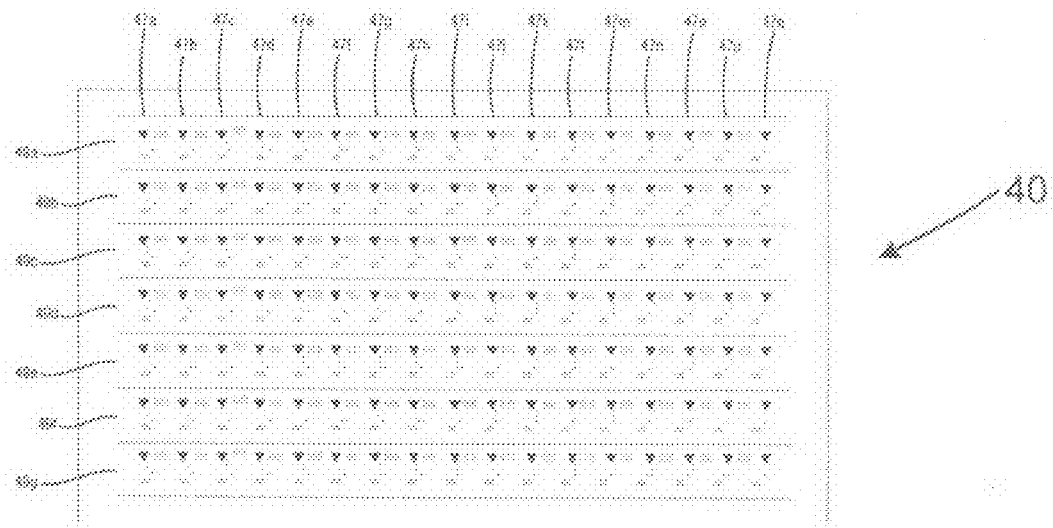
FIG. 8 is a schematic view of the display member circuitry.

The display member 40 is preferably a light emitting diode ("LED"). Alternatively, the display member 40 is a liquid crystal display ("LCD") or other similar display device. As shown in FIG. 8, the display member 40 is an LED array which preferably has seven rows 49a-49g and seventeen columns 47a-47q. Further, LED array is angled to allow for a greater aspect ratio. The LED array allows for each column to be illuminated separately thereby giving the appearance of a moving display. For example, if the term "200 calories expended" is displayed on the display member 40, the "2" of the "200" would preferably first appear in column 47q and then subsequently in each of the other columns 47p-47a, from the right-most column to the left-most column thereby giving the appearance of the term scrolling along the display member 40. The terms or words alternatively scroll from left to right. Still alternatively, all of the columns are illuminated at once or all flash in strobe like manner. Further, the user's real-time pulse waveform is displayed in motion on the display member 40 as a default setting. Those skilled in the pertinent art will recognize alternative methods of displaying information on the display member 40 without departing from the scope and spirit of the present invention.

Figure 9:
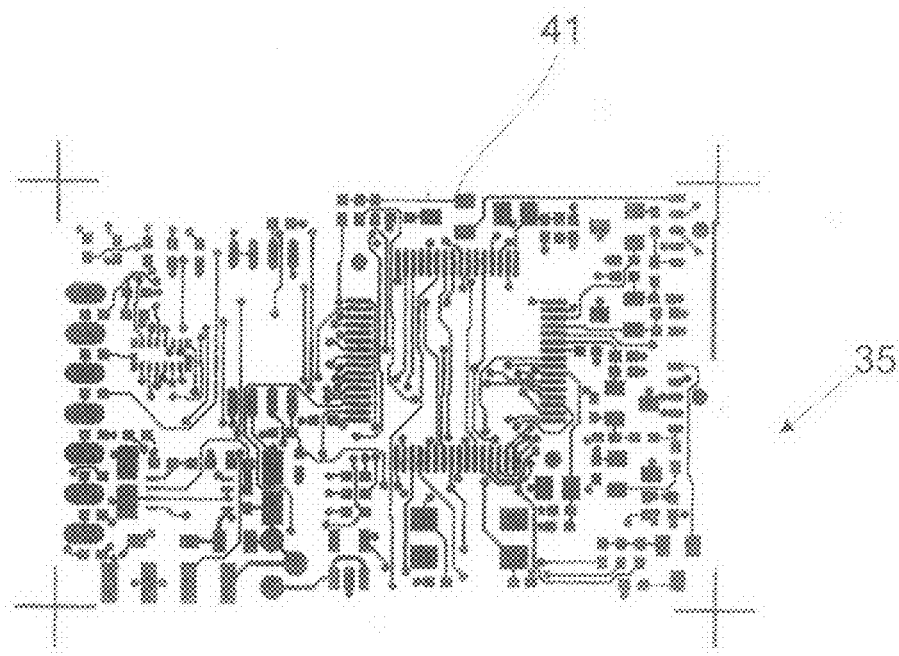
FIG. 9 is a schematic view of the circuitry assembly.

As shown in FIG. 9, a microprocessor 41 processes the signal generated from the optical sensor 30 to generate the plurality of vital sign information for the user which is displayed on the display member 40. The control components 43a-c are connected to the circuit assembly 35 to control the input of information and the output of information displayed on the display member 40.

The monitoring device 20 is preferably powered by a power source 360 positioned on the article 25. Preferably the power source is a battery. The power source 360 is preferably connected to the circuit assembly 35 by positive wire 45a and ground wire 45b, and the ground wire 45b and positive wire 45c are embedded within the article 25. The power source 360 is preferably an AA or AAA disposable or rechargeable battery. The power source 360 is alternatively a lithium ion rechargeable battery such as available from NEC-Tokin. The power source 360 preferably has an accessible port for recharging. The circuit assembly 35 preferably requires 5 volts and draws a current of 20- to 40 milliamps. The power source 360 preferably provides at least 900 milliamp hours of power to the monitoring device 20.

Figure 3:
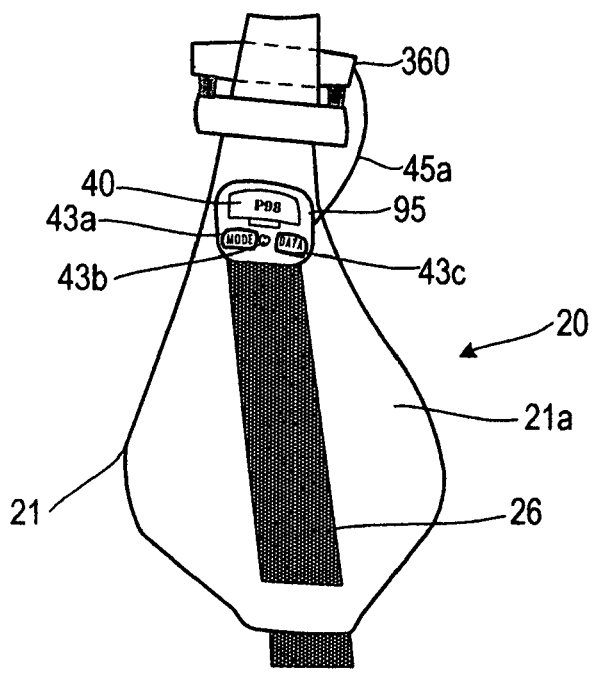
FIG. 3 is a top view of an alternative embodiment of the monitoring device of the present invention.
Figure 3A:
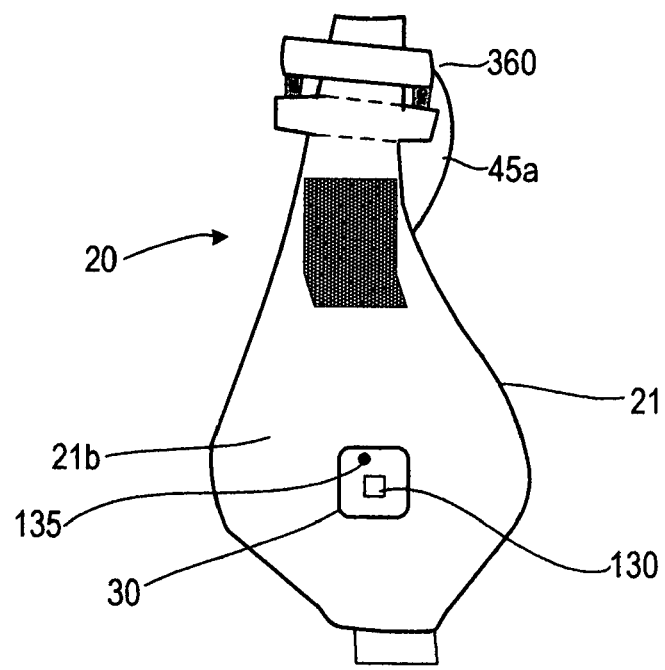
FIG. 3A is bottom view of the monitoring device of FIG. 3.
Figure 3B:
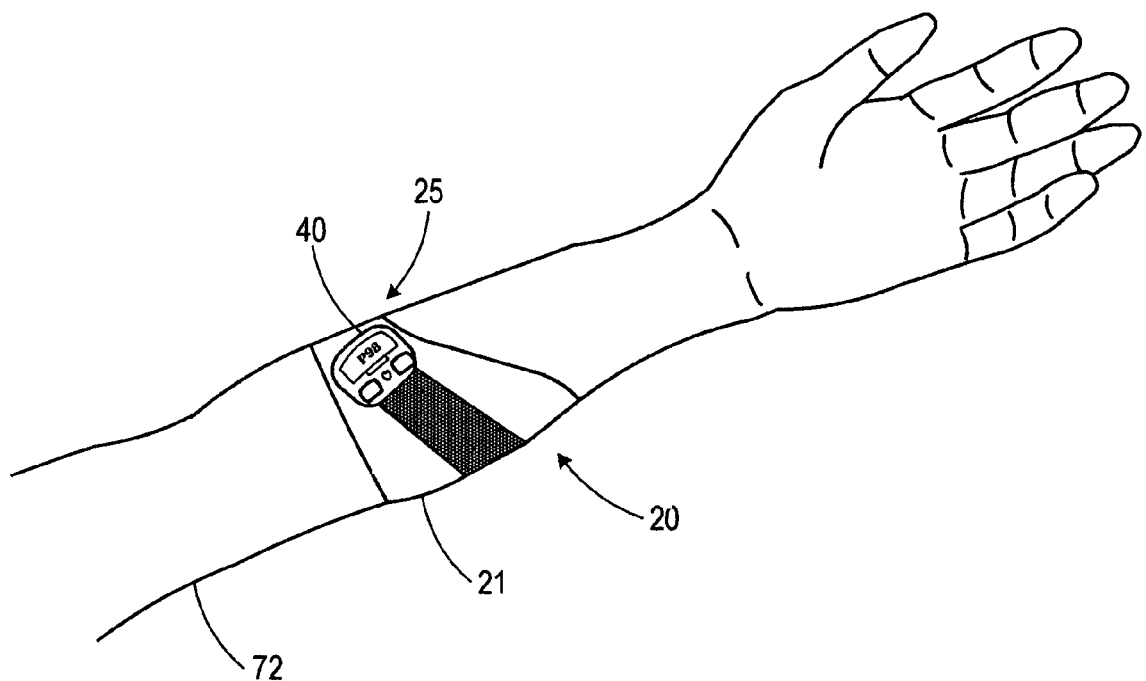
FIG. 3B is a top perspective view of the monitoring device of FIG. 3 worn on a user's arm.

As shown in FIGS. 3, 3A and 3B, an alternative embodiment of the monitoring device 20 comprises a light shield 21 with the article 25 disposed on an exterior surface 21a of the light shield 21, and the optical sensor 30 disposed on an interior surface 21b of the light shield 21. The light shield 21 is preferably composed of a light-weight, non-transparent (preferably opaque) cloth material. The light shield 21 prevents or substantially eliminates environmental light from interfering with the optical sensor 30 thereby reducing interference with the signal. In a preferred embodiment, the light shield 21 is black in color. A user preferably wears the monitoring device 20 on the user's arm 72 as shown in FIG. 3B, with a display member 40 visible to the user. In this embodiment, the article 25 contains a circuitry assembly 35, as discussed above, within the housing 95 of the article 25. The display member 40 is preferably a LED display monitor, and alternatively a LCD display monitor.

Figure 15:
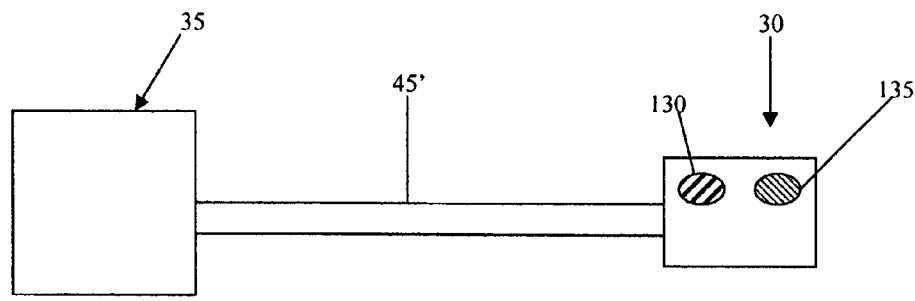
FIG. 15 is a schematic diagram of a prior art connection of a processor to an optical sensor.
Figure 16:
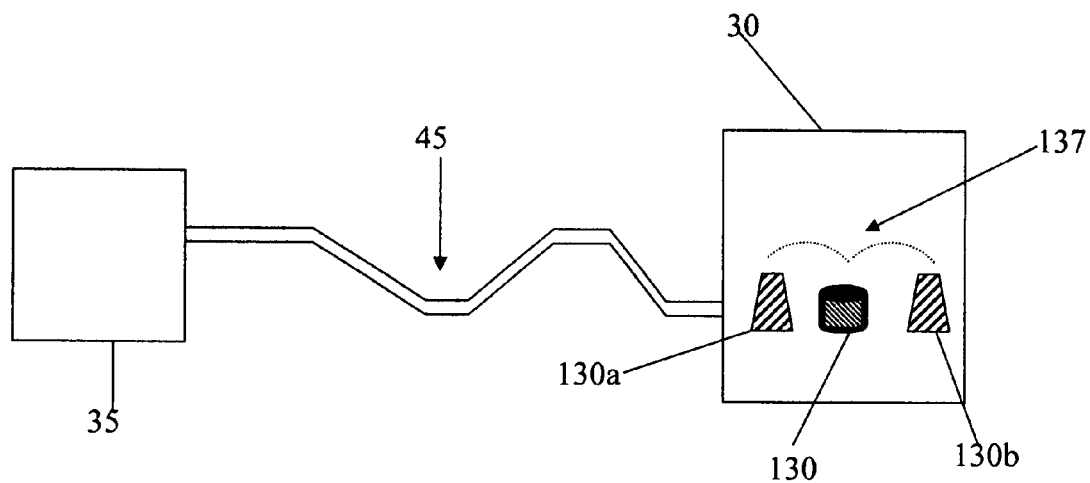
FIG. 16 is a schematic diagram of a connection of a processor to an optical sensor utilized by the present invention.

A connection wire arrangement 45 is shown in FIG. 16, wherein the connection 45 between the microprocessor 41 of the circuitry assembly 35 and the optical sensor 30 is preferably non-planar or non-straight in order to reduce noise in the signal. The optical sensor 30 preferably comprises a photodetector 130, and first and second LEDs 130a and 130b, which transmit light 137. Using two LEDs on each side of a photodetector creates a more mechanically stable optical sensor 30. The prior art connection assembly is shown in FIG. 15 wherein the connection wire 45' is straight and prone to noise due to movement of the circuitry assembly 35 relative to the optical sensor 30, especially lateral movement. The present invention has a non-straight or non-planar connection wire 45 which reduces noise due to movement of the circuitry assembly 35 relative to the optical sensor 30. The alternating portions of the connection wire 45 absorb the shock of lateral movement and oscillating movement of the circuitry assembly 35 relative to the optical sensor 30.

The monitoring device 20 alternatively has a short-range wireless transceiver 36b which is preferably a transmitter operating on a wireless protocol, e.g. BLUETOOTH, part-15, or 802.11. "Part-15" refers to a conventional low-power, short-range wireless protocol, such as that used in cordless telephones. The short-range wireless transmitter 36b (e.g., a BLUETOOTH transmitter) receives information from the microprocessor and transmits this information in the form of a packet through an antenna. An external laptop computer or hand-held device features a similar antenna coupled to a matched wireless, short-range receiver that receives the packet. In certain embodiments, the hand-held device is a cellular telephone with a Bluetooth circuit integrated directly into a chipset used in the cellular telephone. In this case, the cellular telephone may include a software application that receives, processes, and displays the information. The secondary wireless component may also include a long-range wireless transmitter that transmits information over a terrestrial, satellite, or 802.11-based wireless network. Suitable networks include those operating at least one of the following protocols: CDMA, GSM, GPRS, Mobitex, DataTac, iDEN, and analogs and derivatives thereof. Alternatively, the handheld device is a pager or PDA.

Figure 5:
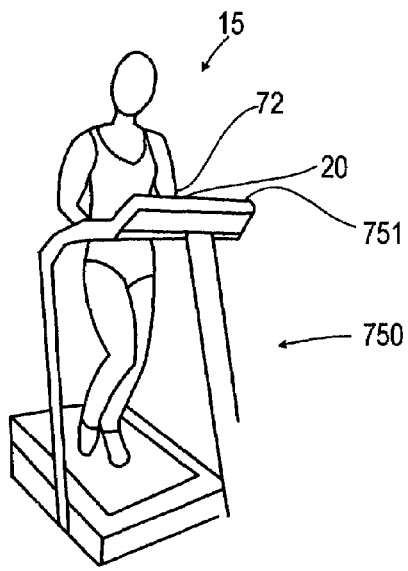
FIG. 5 is a front view of a user running on exercise equipment with the monitoring device on her arm.
Figure 6:
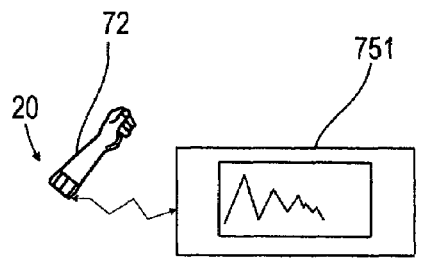
FIG. 6 is an isolated view of a display unit of the exercise equipment of FIG. 5.

As shown in FIGS. 5 and 6, in yet an alternative system utilizing the monitoring device 20, a user 15 wears the monitoring device 20 on the user's arm while exercising on exercise equipment 750. In this embodiment, a wireless signal is transmitted to the exercise equipment 750 to be displayed on a display 751 of the exercise equipment 750. In this embodiment, it is unnecessary for the monitoring device 20 to have a display 40 since the information is transmitted to the exercise equipment 750. As shown in FIG. 5, a user 15 preferably wears the monitoring device 20 on her arm 72 over the radial artery.

A general method is as follows. The light source 135 transmits light through at least one artery of the user. The photo-detector 130 detects the light. The pulse rate is determined by the signals received by the photo-detector 130. An optical sensor 30 with a photodetector 130 and LEDs 135 are preferably utilized.

This information is sent to the circuitry assembly 35 for creation of user's real-time pulse rate. The microprocessor 41 further processes the information to display pulse rate, calories expended by the user of a pre-set time period, target zones of activity, time and/or dynamic blood pressure. The information is displayed on a display member or electro-optical display.

In a preferred embodiment, the housing 95 has three control buttons 43a-c. The control buttons 43a-c are preferably positioned in relation to the display member 40 to allow the user immediate visual feedback of the user's inputted information. The middle control button 43b preferably activates and deactivates the article 25. The left button 43a is preferably used to scroll through the different modes. The right button 43c is preferably used to input data. The control buttons 43a-c allow for the user's personal data to be entered and for choices to be selected by the user. The left button 43a preferably allows for the user's calories burned to be displayed on the display member 40 and for the activity to be reset, and allows for other fitness monitoring features to be displayed.

To activate the article 25, the middle button 43b is depressed for preferably 0.5 seconds and then released. The display member will appear with a current pulse of the user and a calories burned display. The microprocessor preferably stores the calories burned and accumulates the values for a daily calories burned value and a total calories burned value until the activity is reset.

To enter the user's personal data, the middle button 43b is depressed for 2 seconds and then released. The user will enter gender, age, mass, height and resting heart rate. Entering the data entails pushing the middle button to select a category (gender, age, . . . ) and then pushing the right or left button to scroll through the available options or to enter a value (e.g. age of the user). The middle button 43b is pressed again to save the entry. This process is preformed until the user's has entered all of the data that the user wishes to enter into the microprocessor. The display member 40 will then display a heart rate and current calories burned value. A preset resting heart rate for men and women is preferably stored on the microprocessor, and used as a default resting heart rate. However, the user may enter their own resting heart rate value if the user is aware of that value. To access daily calories, the left button 43a is pushed by the user and the display member 40 will illustrate the value for daily calories burned by the user. If the left button 43a is pushed again, the value for total calories burned by the user will be displayed on the display member 40. The left button 43a is pushed again to return to a heart rate value on the display member 40.

The right button 43c is pushed to scroll through the choices of other output values, which comprises: basal metabolic rate; average heart rate; minimum heart rate; maximum heart rate; fat burn heart rate exercise target zone; cardio burn heart rate exercise target zone; and, summary of daily calories burned. The basal metabolic rate (displayed as "BMR") is an estimate of the total calories burned by the user in one day without exercise, and is based on the user inputted personal data. The average heart rate (displayed as "avHR") is the average heart rate of the user between resets, and is an overall indicator of fitness. The lower the average heart rate, the healthier the heart. The average heart rate is also a measure of the effectiveness of the exercise program employed by the user since a decrease in the average heart rate of the user will indicate the user's fitness has improved. The minimum heart rate (displayed as "mnHR") of the user is typically measured during sleep and periods of relaxation. The maximum heart rate (displayed as "mxHR") is typically measured during intense workouts. The fat burn heart rate exercise target zone (displayed as "fatB") displays a low and high range for the heart rate of the user to optimize fat burning during exercise. The cardio burn heart rate exercise target zone provides a high and low range for the heart rate of the user to optimize cardio conditioning during exercise. The summary of daily calories burned (displayed as "cal") displays the daily calories burned by the user.

In yet an alternative embodiment, an accelerometer, not shown, is embedded within the article 25 and connected to the circuitry assembly 35 in order to provide information on the distance traveled by the user. In a preferred embodiment, the accelerometer is a multiple-axis accelerometer, such as the ADXL202 made by Analog Devices of Norwood, Mass. This device is a standard micro-electronic-machine ("MEMs") module that measures acceleration and deceleration using an array of silicon-based structures.

In yet another embodiment, the monitoring device 20 comprises a first thermistor, not shown, for measuring the temperature of the user's skin and a second thermistor, not shown, for measuring the temperature of the air. The temperature readings are displayed on the display member 40 and the skin temperature is preferably utilized in further determining the calories expended by the user during a set time period. One such commercially available thermistor is sold under the brand LM34 from National Semiconductor of Santa Clara, Calif. A microcontroller that is utilized with the thermistor is sold under the brand name ATMega 8535 by Atmel of San Jose, Calif.

The monitoring device 20 may also be able to download the information to a computer for further processing and storage of information. The download may be wireless or through cable connection. The information can generate an activity log or a calorie chart.

The microprocessor can use various methods to calculate calories burned by a user. One such method uses the Harris-Benedict formula. Other methods are set forth at www.un-u.edu/unupress/food2/ which relevant parts are hereby incorporated by reference. The Harris-Benedict formula uses the factors of height, weight, age, and sex to determine basal metabolic rate (BMR). This equation is very accurate in all but the extremely muscular (will underestimate calorie needs) and the extremely overweight (will overestimate caloric needs) user.

The equations for men and women are set forth below:

Men: BMR=66+(13.7×mass(kg))+(5×height(cm))−(6.8×age(years))

Women: BMR=655+(9.6×mass)+(1.8×height)−(4.7×age)

The calories burned are calculated by multiplying the BMR by the following appropriate activity factor: sedentary; lightly active; moderately active; very active; and extra active.

Sedentary=BMR multiplied by 1.2 (little or no exercise, desk job)

Lightly active=BMR multiplied by 1.375 (light exercise/sports 1-3 days/wk)

Moderately Active=BMR multiplied by 1.55 (moderate exercise/sports 3-5 days/wk)

Very active=BMR multiplied by 1.725 (hard exercise/sports 6-7 days/wk)

Extra Active=BMR multiplied by 1.9 (hard daily exercise/sports & physical job or 2× day training, marathon, football camp, contest, etc.)

Various target zones may also be calculated by the microprocessor. These target zones include: fat burn zone; cardio zone; moderate activity zone; weight management zone; aerobic zone; anaerobic threshold zone; and red-line zone.

Fat Burn Zone=(220−age)×60% & 70%

An example for a thirty-eight year old female:
i. (220−38)×0.6=109
ii. (220−38)×0.7=127
iii. Fat Burn Zone between 109 to 127 heart beats per minute.

Cardio Zone=(220−your age)×70% & 80%

An example for a thirty-eight year old female:
i. (220−38)×0.7=127
ii. (220−38)×0.8=146
iii. Cardio zone is between 127 & 146 heart beats per minute.

Moderate Activity Zone, at 50 to 60 percent of your maximum heart rate, burns fat more readily than carbohydrates. That is the zone one should exercise at if one wants slow, even conditioning with little pain or strain.

Weight Management Zone, at 60 to 70 percent of maximum, strengthens ones heart and burns sufficient calories to lower one's body weight.

Aerobic Zone, at 70 to 80 percent of maximum, not only strengthens one's heart but also trains one's body to process oxygen more efficiently, improving endurance.

Anaerobic Threshold Zone, at 80 to 90 percent of maximum, improves one's ability to rid one's body of the lactic-acid buildup that leads to muscles ache near one's performance limit. Over time, training in this zone will raise one's limit.

Red-Line Zone, at 90 to 100 percent of maximum, is where serious athletes train when they are striving for speed instead of endurance.

EXAMPLE ONE

Female, 30 yrs old, height 167.6 centimeters, weight 54.5 kilograms.

The BMR=655+523+302−141=1339 calories/day.

The BMR is 1339 calories per day. The activity level is moderately active (work out 3-4 times per week). The activity factor is 1.55. The TDEE=1.55×1339=2075 calories/day. TDEE is calculated by multiplying the BMR of the user by the activity multiplier of the user.

The heart rate may be used to dynamically determine an activity level and periodically recalculate the calories burned based upon that factor. An example of such an activity level look up table might be as follows:

Activity/Intensity Multiplier Based on Heart Rate

Sedentary=BMR×1.2 (little or no exercise, average heart rate 65–75 bpm or lower)

Lightly active=BMR×3.5 (light exercise, 75 bpm-115 bpm)

Mod. active=BMR×5.75 (moderate exercise, 115-140 pm)

Very active=BMR×9.25 (hard exercise, 140-175 bpm)

Extra active=BMR×13 (175 bpm–maximum heart rate as calculated with MHR formula)

For example, while sitting at a desk, a man in the above example might have a heart rate of between 65 and 75 beats per minute (BPM). (The average heart rate for an adult is between 65 and 75 beats per minute.) Based on this dynamically updated heart rate his activity level might be considered sedentary. If the heart rate remained in this range for 30 minutes, based on the Harris-Benedict formula he would have expended 1.34 calories a minute×1.2 (activity level)×30 minutes, which is equal to 48.24 calories burned.

If the man were to run a mile for 30 minutes, with a heart rate ranging between 120 and 130 bpm, his activity level might be considered very active. His caloric expenditure would be 1.34 calories a minute×9.25 (activity level)×30 minutes, which is equal to 371.85.

Another equation is weight multiplied by time multiplied by an activity factor multiplied by 0.000119.

Figure 7:
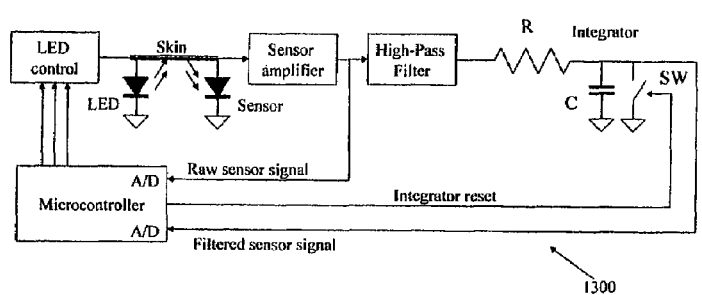
FIG. 7 is a schematic flow chart of the signal acquisition step of the flow chart of FIG. 10.
Figure 10:
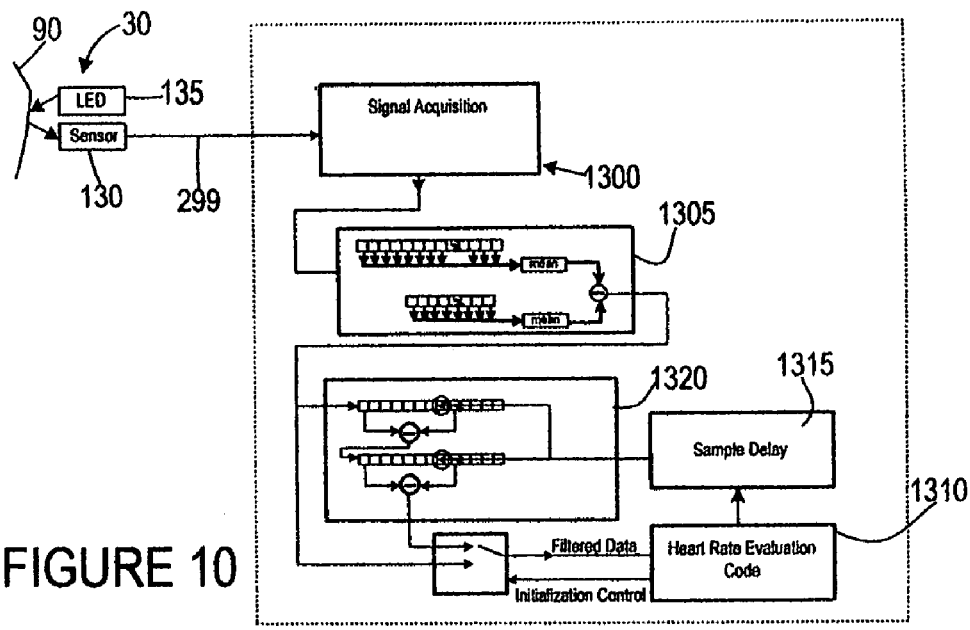
FIG. 10 is a flow chart of a signal processing method of the present invention.
Figure 11:
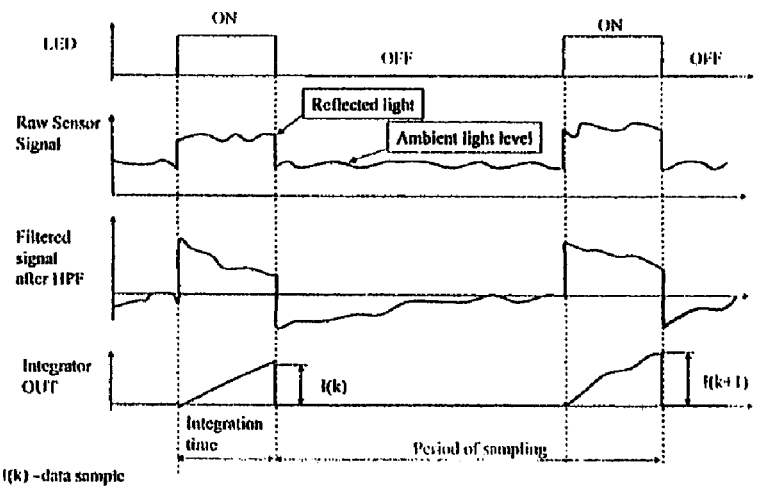
FIG. 11 is an illustration of the waveforms of the data sampling during the signal processing method.

FIG. 10 illustrates a block diagram of a flow chart of a signal processing method of the present invention. As shown in FIG. 10, the photodetector 130 of the optical sensor 30 receives light from the light source 135 while in proximity to the user's artery. The light source 135 is preferably a plurality of LEDs 135. In a preferred embodiment, the optical sensor 30 is a TRS1755 which includes a green LED light source (567 nm wavelength) and a light-to-voltage converter. The output voltage is directly proportional to the reflected light intensity. The signal 299 is sent to the microprocessor 41. At block 1300, the signal acquisition is performed. As shown in FIG. 7, in the pulse mode the LED 135 is periodically activated for short intervals of time by a signal from the microcontroller. The reflected pulse of light is received by the sensor, with the generation of a voltage pulse having an amplitude proportional to the intensity of the reflected light. When the LED is activated, the switch, SW, is open by the action of the control signal from the microcontroller, and the capacitor, C, integrates the pulse generated from the sensor by charging through the resistor R. Immediately prior to deactivation of the LED, the analog-to-digital converter acquires the value of the voltage integrated across the capacitor, C. The analog-to-digital converter generates a data sample in digital form which is utilized by the microcontroller for evaluation of the heart rate the wearer. Subsequent to the sample being acquired by the analog-to-digital converter, the LED is deactivated and the capacitor, C, is shortcut by switch, SW, to reset the integrator, RC. A signal indicating sensor saturation is also sent to the microcontroller for light control of the LEDs. This states remains unchanged for a given time interval after which the process is repeated, which is illustrated in FIG. 11. The signals are shown in FIG. 11, with the raw sensor signal received from the sensor amplifier shown as varying between reflected light when the LEDs are on and an ambient light level when the LEDs are off. The filtered signal from the high pass filter ("HPF") is shown as the filtered sensor signal in FIG. 7. The integrator reset signal is shown as integrator out signal in FIG. 11, and the integrator reset signal in FIG. 7. A noise reduction and power reduction process is discussed below in reference to FIGS. 13 and 14.

At block 1305, a band pass filter is implemented preferably with two sets of data from the analog-to-digital converter. At block 1305, an average of the values of data samples within each of a first set of samples is calculated by the microprocessor. For example, the values of data samples within forty-four samples are summed and then divided by forty-four to generate an average value for the first set of samples. Next, an average of the values of data samples within a second set of samples is calculated by the microprocessor. For example, the values of data samples within twenty-two samples are summed and then divided by twenty-two to generate an average value for the second set of samples. Preferably, the second set of samples is less than the first set of samples. Next, the average value of the second set of samples is subtracted from the average value for the first set of samples to generate a first filtered pulse data value.

At block 1310, the filtered pulse data value is processed using a heart rate evaluation code to generate a first heart rate value. In a preferred method, the heart rate evaluation code obtains the heart rate by calculating the distance between crossing points of the voltage through zero. Once the first heart rate value is known, then an adaptive resonant filter is utilized to generate a filtered second heart rate value by attenuating interference caused by motion artifacts. At block 1315, a sample delay is computed as the period of evaluated heart rate divided by two.

At block 1320, preferably a two cascade adaptive resonant filter generates a second filtered pulse data value which is processed at block 1310 using the heart rate evaluation code to generate a second heart rate value. Those skilled in the pertinent art will recognize that three, four, or more, cascade adaptive resonant filters may be utilized in generating the second filtered pulse data value. Essentially, the highest and lowest values are disregarded in calculating the filtered second heart rate value. Alternatively, a phase is established and any values outside of the phase are disregarded in calculating the second heart rate value. The filtering is preferably continued during the use of the monitor thereby further refining the heart rate value of the user.

Figure 12:
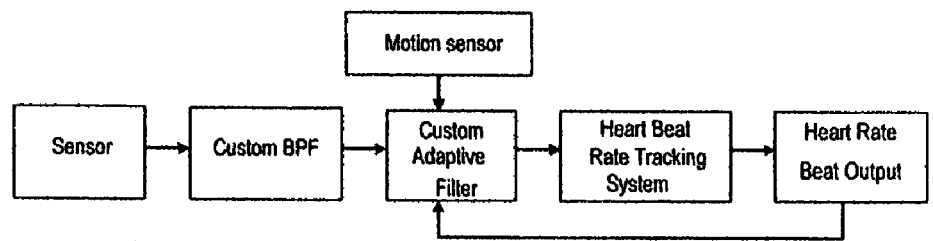
FIG. 12 is a flow chart of a portion of the signal processing step utilizing a motion sensor to reduce the affect of motion.

As shown in FIG. 12, a motion sensor 1100 is included in an alternative embodiment to assist in identifying motion noise and filtering the noise from the signal sent by the sensor 30. The motion sensor 1100, such as an accelerometer, is integrated into the circuitry and software of the monitoring device 20. As the motion sensor detects an arm swinging, the noise component is utilized with the signal processing noise filtering techniques to provide additional filtering to remove the noise element and improve the accuracy of the monitoring device 20. More specifically, the signal from the sensor 30 is transmitted to the processor where a custom blood pressure filter 41w processes the signal which is further processed at by custom adaptive filter 41x before being sent to a heart beat tracking system 41y and then transmitted to a heart rate beat output 41z. The heart rate beat output 41z provides feedback to the custom adaptive filter 41x which also receives input from the motion sensor 1100.

Still further, a battery source containing twin AAA batteries is built into a buckle for the straps 26a and 26b. The battery holder is preferably similar in appearance to a shoe buckle.

Figure 13:
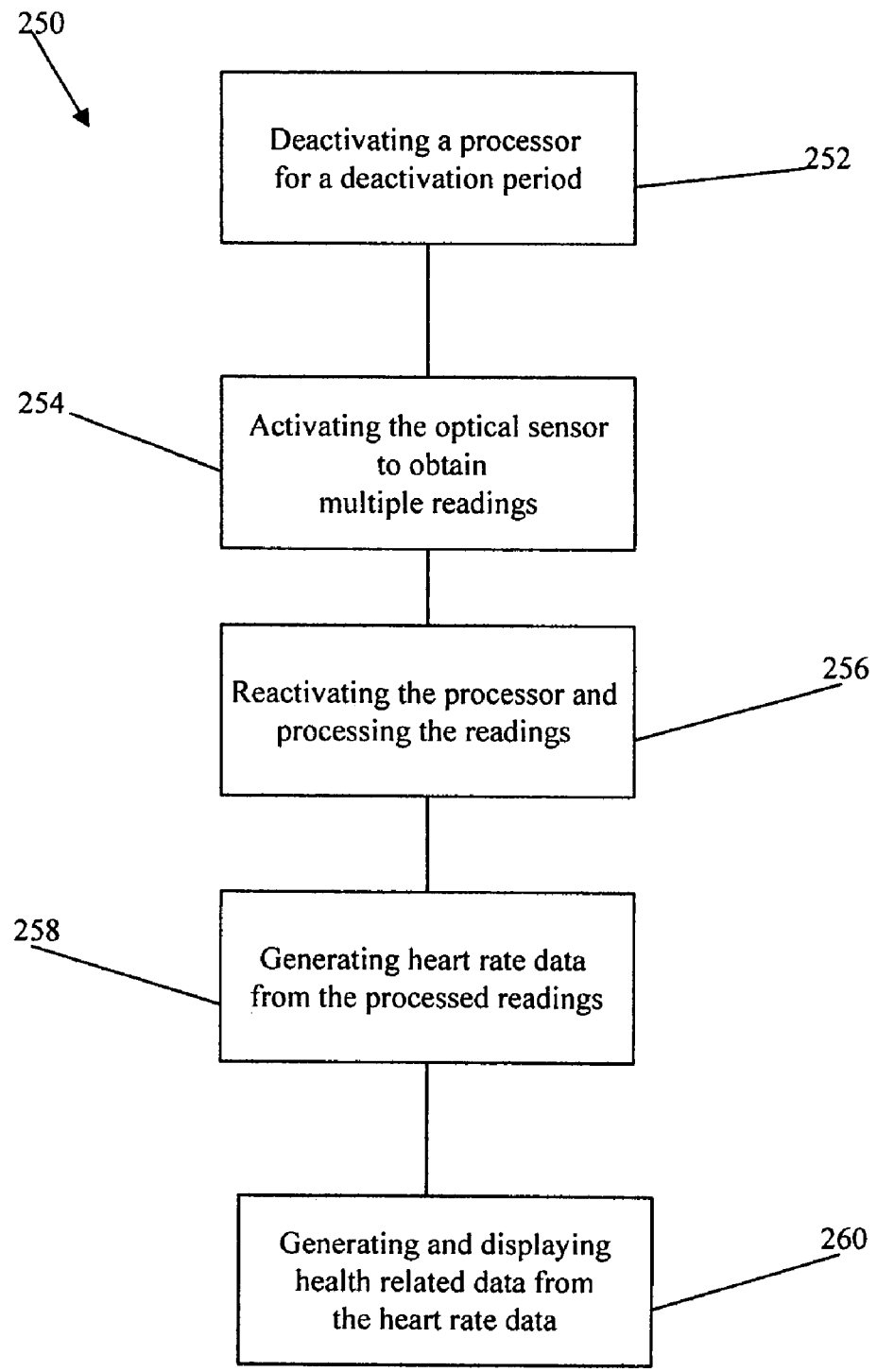
FIG. 13 is a flow chart of a noise reduction method of the present invention.

FIG. 13 illustrates a noise reduction method of the present invention. Due to the desire to minimize power consumption of the monitoring device 20, and achieve very accurate signal measurements using the optical sensor 30, the present invention preferably utilizes the method 200 illustrated in FIG. 13. At block 202, the processor 41 is deactivated for a deactivation period in order to conserve power and to eliminate noise for a signal measurement. The deactivation period ranges from 128 to 640 microseconds, more preferably from 200 microseconds to 400 microseconds, and more preferably from 225 microseconds to 300 microseconds. In reference to FIG. 10, this deactivation period occurs during block 1300. At block 204, during the deactivation period, the optical sensor 30 is activated to obtain multiple readings using the light source 135 and the photodetector 130. Preferably 4 to 25 sub-readings or sub-samples are obtained during the deactivation period. The sub-readings or sub-samples are averaged for noise reduction to provide a reading or sample value. In a single second, from 500 to 1500 sub-readings or sub-samples are obtained by the optical sensor 30. At block 206, the processor 41 is reactivated and the reading values are processed by processor 41. At block 208, heart rate data is generated from the readings by the processor 41. At block 210, health related data is generated from the heart rate data, and the health related data and the heart rate data are displayed on the display member 40.

Figure 14:
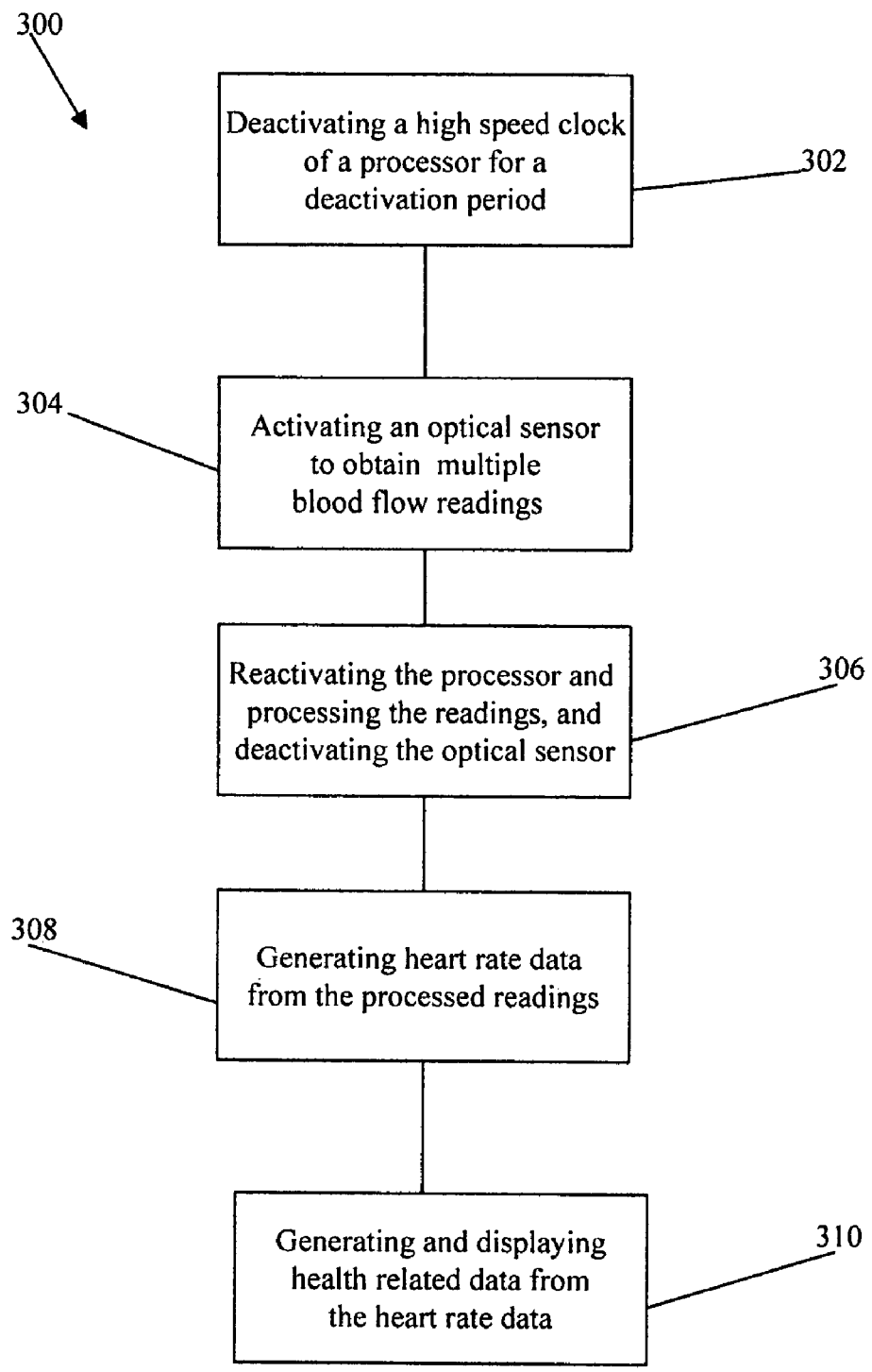
FIG. 14 is a flow chart of a specific noise reduction method of the present invention.

FIG. 14 illustrates a more specific method 300 for noise reduction during a signal reading. At block 302, a high speed clock of a processor 41 is deactivated for a deactivation period as discussed above. At block 304, the optical sensor 30 is activated during the deactivation period to obtain multiple readings as discussed above. At block 306, the processor 41 is reactivated and the readings are processed. The optical sensor 30 is also deactivated. At block 308, heart rate data is generated from the readings by the processor 41. At block 310, health related data is generated from the heart rate data, and the health related data and the heart rate data are displayed on the display member 40.

Figure 17:
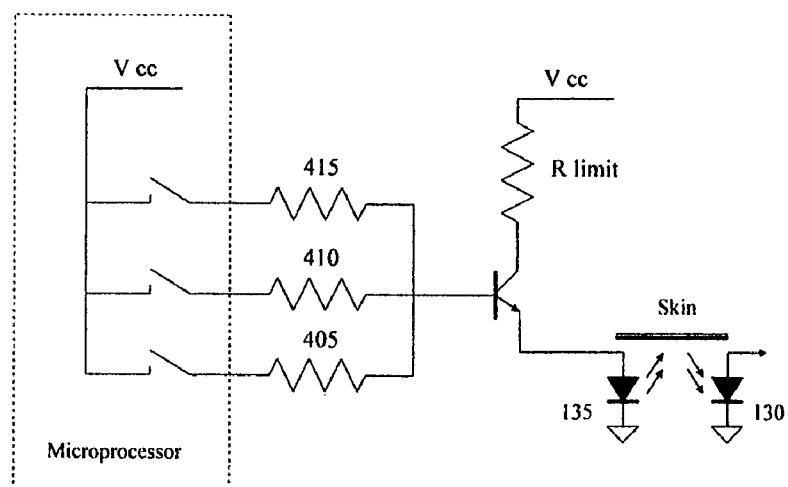
FIG. 17 is a schematic diagram of a light source intensity controlling mechanism of the present invention.

FIG. 17 illustrates a mechanism for controlling the intensity of the light source 135 using a plurality of resistors 405, 410 and 415 in parallel. Usually, an optical sensor 30 has a light source 135 set for a single intensity for placement at a single location on a user. However, if the optical sensor 30 is placed at a different location, e.g. from the lower arm to the upper arm, the intensity of the light source 135 may be too great for the photodetector 130 and lead to saturation of the photodector 130 which terminates the signal reading. The present invention preferably adjusts the intensity of the light source 135 using feedback from the photodetector 130 to indicate whether the light intensity is too high or too low. As shown in FIGS. 17, 17A, 17B and 17C, the current flow through the resistors 405, 410 and 415 is changed, which results in changes in the light intensity of the light source 135. Equation A below illustrates the resistance:

$$1/R_{eff} = S_1(1/R_1) + S_2(1/R_2) + S_3(1/R_3)$$

where $S_n$=Switch$_n$ having a value of 0 or 1, and $R_n$=resistor, in ohms. In one embodiment, resistor 405 has a resistance of 400 Ohms, resistor 410 has a resistance of 200 Ohms and resistor 415 has a resistance of 100 Ohms. Various combinations of the resistors can be switched on to control the light intensity.

Figure 17A:
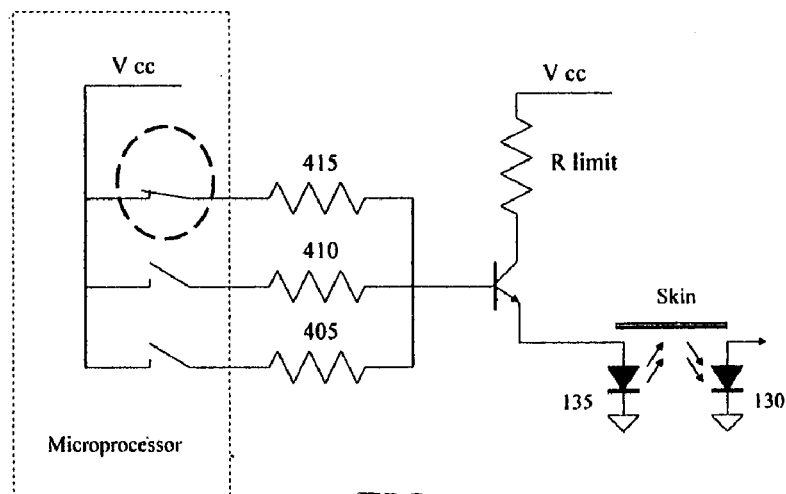
FIG. 17A is a schematic diagram of the light source intensity controlling mechanism of FIG. 17 with a single resistor connected.
Figure 17C:
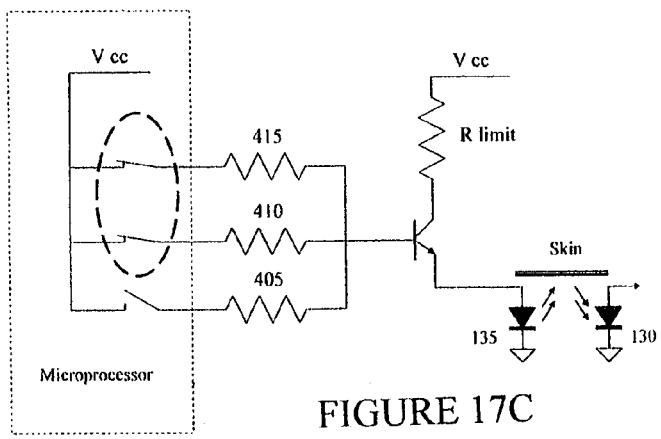
FIG. 17C is a schematic diagram of the light source intensity controlling mechanism of FIG. 17 with two resistors connected.
Figure 17B:
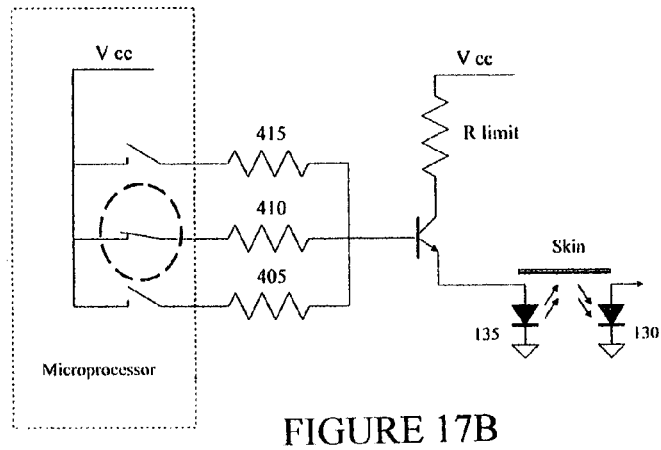
FIG. 17B is a schematic diagram of the light source intensity controlling mechanism of FIG. 17 with a single resistor connected.

FIG. 17A has current flowing through a single line and a single resistor. FIG. 17C has current flowing through all of the lines. Although FIG. 17C utilizes the most resistors 410 and 415, it has the greatest current flow and the highest intensity. The current flow is given by the equation B:

$$(V_{cc} - V)/R_{eff} = I_{LED}$$

where $I_{LED}$ is the current flow. Although only three resistors are shown, those skilled in the pertinent art will recognize the more or fewer resistors may be used without departing from the scope and spirit of the present invention.

Figure 18:
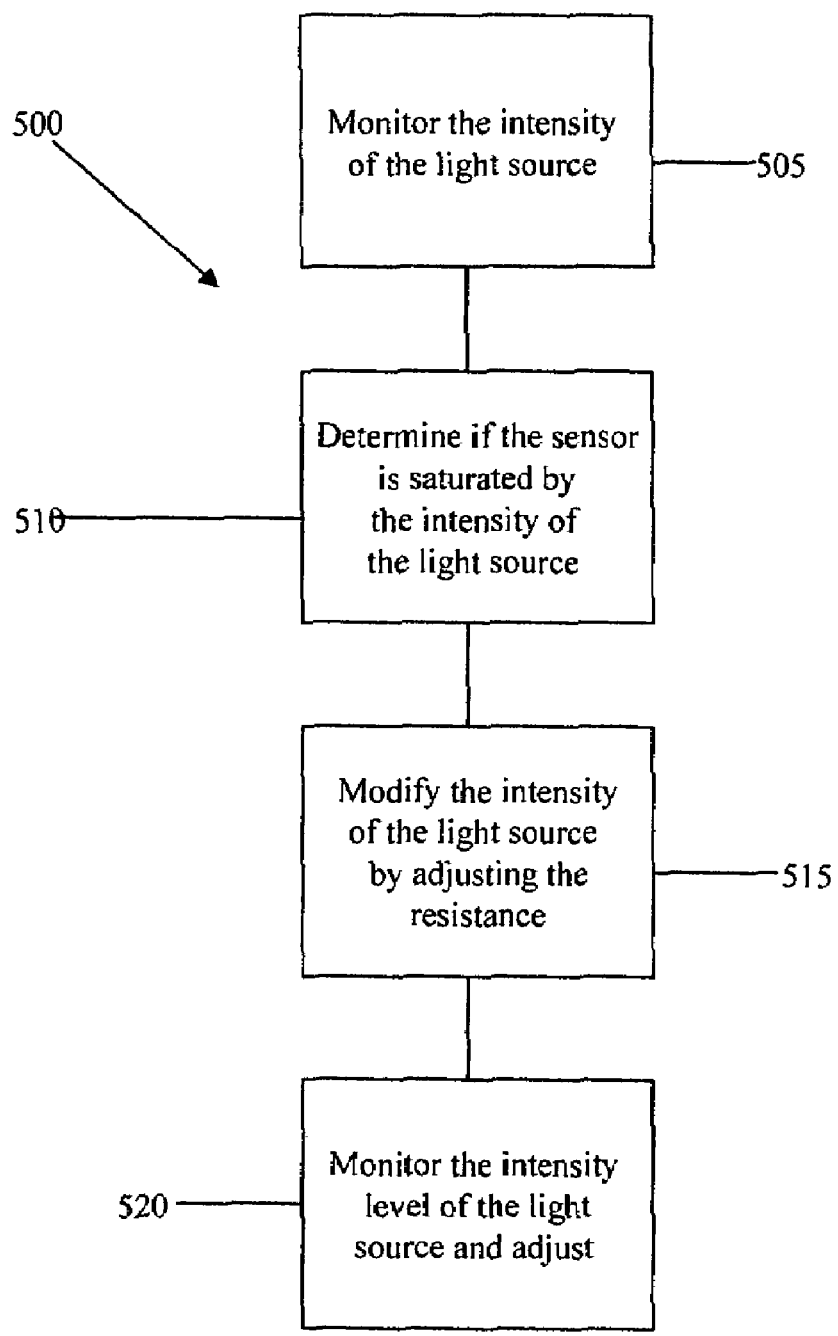
FIG. 18 is a flow chart of a light source intensity controlling method of the present invention.

FIG. 18 is a preferred method 500 for controlling the light intensity of the optical sensor 30. At block 505, the light intensity of the light source 135 is monitored. At block 510, the sensor/phototdetector is determined to be saturated by the light source. At block 515, the intensity of the light source is modified by adjusting the resistance and the flow of current to the light source 135. At block 520, the light intensity is again monitored and adjusted if necessary. In a preferred embodiment, this automatic gain mechanism prevents the green light from overwhelming the photodetector thereby maintaining an accurate reading no matter where the optical sensor is placed on the user.

Figure 19:
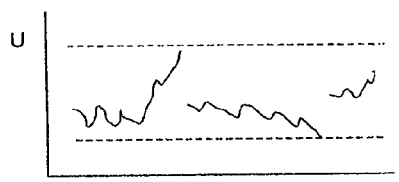
FIG. 19 is a graph illustrating the method and mechanism of controlling the intensity of the light source over time.

FIG. 19 illustrates how the control mechanism operates to maintain a proper light intensity. As the signal reaches the upper limit, the photodetector becomes saturated and the processor lowers the current flow, which results in a break in the signal. Then as the signal is lowered it becomes too low and the processor increases the light intensity resulting in a break in the signal.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention:

1. A method of monitoring a user's vital signs, the method comprising:
   deactivating a processor for a deactivation period of 128 to 640 microseconds;
   activating an optical sensor during the deactivation period to generate a signal corresponding to the flow of blood through at least one artery of the user, the optical sensor comprising a photodetector and a plurality of light-emitting diodes;
   reactivating the processor to process the signal to obtain an average pulse value of a first set of time periods;
   processing the signal to obtain an average pulse value of a second set of time periods, the second set of time periods less than the first set of time periods;
   subtracting the average pulse value of the second set of time periods from the average pulse value of the first set of time periods to generate a first filtered pulse data value;
   processing the first filtered pulse data value to obtain a first heart rate value;
   using the first heart rate value to filter the subsequent average pulse values generated from the digital signal to obtain a real-time heart rate value of the user;
   processing the real-time heart rate data of the user for analysis of real-time calories expended by the user and for real-time display of a plurality of the user's vital signs; and
   displaying the plurality of user's vital signs on a display member, the display of the plurality of user's vital signs controlled by the user using a control component.

2. The method according to claim 1 further comprising filtering motion noise from the signal utilizing a motion sensor.

3. The method according to claim 1 wherein the plurality of light emitting diodes comprises a plurality of pulsed infrared light emitting diodes.

4. The method according to claim 1 wherein the plurality of light emitting diodes comprises a pulsed infrared light emitting diode and a green light emitting diode.

5. The method according to claim 1 wherein the real-time heart rate data is based on 60 to 180 sample readings and each of the sample readings is based on 4 to 15 sub-sample readings.

6. The method according to claim 1 wherein the processor, the optical sensor and the display member are disposed on a monitoring device.

* * * * *